(12) United States Patent
Fromentin et al.

(10) Patent No.: US 10,308,618 B2
(45) Date of Patent: Jun. 4, 2019

(54) BLUE LIGHT CUTTING OPTICAL MATERIAL COMPRISING A BENZOTRIAZOLE UV ABSORBER

(71) Applicant: ESSILOR INTERNATIONAL, Charenton-le-Pont (FR)

(72) Inventors: Pierre Fromentin, Bangkok (TH); Tipparat Lertwattanaseri, Bangkok (TH)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 16/076,426

(22) PCT Filed: Feb. 7, 2017

(86) PCT No.: PCT/EP2017/052595
§ 371 (c)(1),
(2) Date: Aug. 8, 2018

(87) PCT Pub. No.: WO2017/137372
PCT Pub. Date: Aug. 17, 2017

(65) Prior Publication Data
US 2019/0047967 A1    Feb. 14, 2019

(30) Foreign Application Priority Data
Feb. 8, 2016    (EP) .................................... 16305149

(51) Int. Cl.
| | | |
|---|---|---|
| *C07D 249/20* | (2006.01) | |
| *G02B 1/04* | (2006.01) | |
| *C08F 220/36* | (2006.01) | |
| *C08F 20/36* | (2006.01) | |

(52) U.S. Cl.
CPC ............ *C07D 249/20* (2013.01); *C08F 20/36* (2013.01); *C08F 220/36* (2013.01); *G02B 1/043* (2013.01)

(58) Field of Classification Search
CPC .............................. C07D 249/20; G02B 1/043
See application file for complete search history.

(56) References Cited

U.S. PATENT DOCUMENTS

| | | |
|---|---|---|
| 4,716,234 A | 12/1987 | Dunks et al. |
| 6,096,846 A | 8/2000 | Oda et al. |

FOREIGN PATENT DOCUMENTS

| | | |
|---|---|---|
| EP | 2963457 | 1/2016 |
| EP | 3056545 | 8/2016 |
| JP | H11-271501 | 10/1999 |
| JP | 2000-147201 | 5/2000 |
| JP | 2004-345123 | 12/2004 |
| JP | 2008-056854 | 3/2008 |
| JP | 2014-071484 | 4/2014 |
| WO | WO 2007/050395 | 5/2007 |

OTHER PUBLICATIONS

International Search Report and Written Opinion issued in International Patent Application No. PCT/EP2017/052595, dated Apr. 12, 2017.

*Primary Examiner* — Golam M Shameem
(74) *Attorney, Agent, or Firm* — Norton Rose Fulbright US LLP

(57) ABSTRACT

Optical material comprising a polymer matrix and at least one benzotriazole compound having at least one ester group, wherein said at least one benzotriazole is a chlorobenzotriazole compound that does not comprise any polymerizable group selected from allylic, acrylic and methacrylic moieties, or the optical transmittance through a 2 mm thick layer of said optical material is lower than 1% for each light wavelength ranging from 280 to 400 nm, and higher than 65% for light having a wavelength of 430 nm. This optical material can be used to protect from phototoxic blue light and UV light.

16 Claims, 1 Drawing Sheet

BLUE LIGHT CUTTING OPTICAL MATERIAL COMPRISING A BENZOTRIAZOLE UV ABSORBER

CROSS-REFERENCE TO RELATED APPLICATIONS

Figure 1:
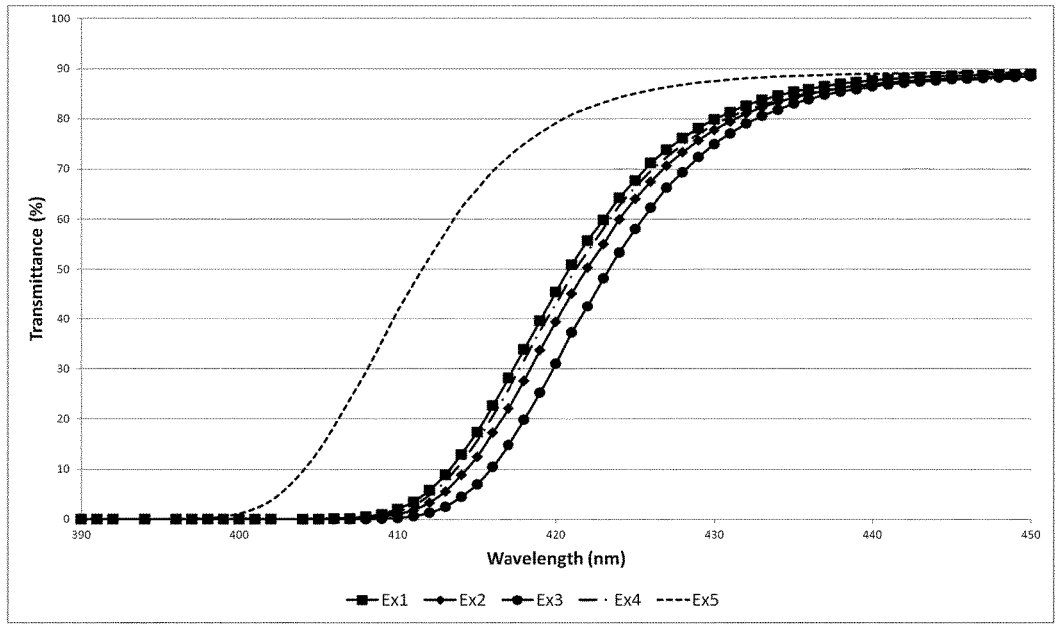

This application is a national phase application under 35 U.S.C. § 371 of International Application No. PCT/EP2017/052595 filed 7 Feb. 2017, which claims priority to European Patent Application No. 16305149.3 filed 8 Feb. 2016. The entire contents of each of the above-referenced disclosures is specifically incorporated by reference herein without disclaimer.

The present invention relates to optical materials comprising compounds that absorb UV light and at least part of the blue light of the visible spectrum, and more particularly to ophthalmic lenses containing these materials. The present invention is also directed to methods of making these materials.

Light that is visible to humans extends over a light spectrum ranging from a 380 nanometers (nm) wavelength to a 780 nm wavelength approximately. The part of this spectrum, ranging from around 380 nm to around 500 nm, corresponds to a high-energy, essentially blue light.

Many studies (see for example Kitchel E., "The effects of blue light on ocular health", Journal of Visual Impairment and Blindness Vol. 94, No. 6, 2000 or Glazer-Hockstein and al., Retina, Vol. 26, No. 1. pp. 1-4, 2006) suggest that part of the blue light has phototoxic effects on the human eye health, and especially on the retina. Ocular photobiology studies demonstrated that an excessively prolonged or intense exposure to blue light may induce severe ophthalmic diseases such as age-related macular degeneration (ARMD) or cataract. Thus, it is recommended to limit the exposure of the eyes to blue light potentially harmful, in particular as regards the wavelength band with an increased dangerousness (420-450 nm).

Eyeglasses are particularly suitable to offer protection against such potentially harmful blue light.

It is furthermore necessary to eliminate as much as possible the harmful influence of ultraviolet light (UV light) on the eye of a wearer of the lens. Ultraviolet (UV) light is the portion of the luminous spectrum below 380 nm and ranging up to 100 nm. The UV spectrum has many bands, especially UVA, UVB and UVC bands. Amongst those UV bands reaching the earth surface, the UVA band, ranging from 315 nm to 380 nm, and the UVB band, ranging from 280 nm to 315 nm, are particularly harmful to the retina.

It has already been suggested to cut at least partially UV light and/or the troublesome part of the blue light spectrum from 400 nm to 460 nm, by means of a filter inhibiting the light in a suitable wavelength range, through absorption or through reflection.

Optical filtering means such as UV absorbers are frequently incorporated in optical articles in order to reduce or prevent UV light from reaching the retina (in particular in ophthalmic lens materials), but also to protect the substrate material itself, thus preventing it from weathering and becoming brittle and/or yellow. The commonly used UV absorbers are benzotriazole and benzophenone derivatives.

The UV absorber can be incorporated into the finished product trough different technologies at different locations, generally in a coating such as a hard coat, but also in the bulk substrate, for example by impregnation of the substrate, or less frequently by incorporation in a substrate precursor formulation.

The Japanese patent application JP 2008-056854 discloses a polymerizable composition for lenses comprising polythiol and polyiso(thio)cyanate monomers and at least one specific benzotriazole-based ultraviolet absorber, wherein the optical cut rate at a wavelength of 400 nm of a 9 mm-thick polythiourethane resin sheet obtained from the composition is 99.5% or more. The benzotriazole UV absorber can be chosen from isooctyl-3-(3-(2H-benzotriazol-2-yl)-5-t-butyl-4-hydroxy-phenylpropionate (Tinuvin® 384), 2-[2-hydroxy-3-(dimethylbenzyl)-5-(1,1,3,3-tetramethylbutyl) phenyl]-2H-benzotriazole (Tinuvin® 928), 2-[2-hydroxy-3,5-bis (dimethylbenzyl) phenyl]-2H-benzotriazole (Tinuvin® 234) and 2-(2-hydroxy-3,5-di-tert-butyl-phenyl)-5-chlorobenzotriazole (Tinuvin® 327).

The Japanese patent application JP 2000-147201 discloses a plastic lens ensuring a high visible radiation transmittance made of a sulfur containing resin (e.g., polythiourethane or polyepisulfide), further containing a high molecular weight UV absorber having miscibility with the base resin, which can be a benzophenone or benzotriazole UV absorber, such as polyethylene glycol monoesters and diesters of 3-[5-(2-benzotriazoyl)-3-t-butyl-4-hydroxyphenyl] propionic acid (UVC2). A UV absorber less liable to absorb yellow, brown, etc., in the visible radiation region is preferably used, leading to a reduced light cut-off wavelength.

The application WO 2014/133111 discloses an optical material containing one or more ultraviolet absorbers having a maximum absorption peak in a range from 350 nm to 370 nm, which is configured to restrict exposure of the eyes of a user to blue light with relatively short wavelengths, specifically in the 400 to 420 nm wavelength range. The benzotriazoles that can be used are 2-(2-hydroxy-3-t-butyl-5-methylphenyl)-chlorobenzotriazole (Seesorb® 703), Tinuvin Carboprotect®, 2-(3,5-di-t-amyl-2-hydroxyphenyl) benzotriazole and 2-(2-hydroxy-5-t-octylphenyl) benzotriazole.

Other substrates containing UV-absorbing benzotriazoles are disclosed in WO 2015/046540 and JP 2004-345123.

Further, UV-absorbing benzotriazole ester structures have been widely used in contact lenses/intraocular lenses, as disclosed in WO 2007/050395 and U.S. Pat. No. 6,096,846, but these structures contain polymerizable (meth)acryloxy functions to ensure reticulation of the UV absorber within the substrate during polymerization.

Incorporating into an optical material composition an optical filtering means able to cut the wavelengths that may present an impact on the health can prove difficult (in particular when it is devoid of cross-linking group), as it is necessary to adapt the formulation of the optical material composition to avoid compatibility issues, in particular with UV absorbers that are prone to precipitation. It is especially difficult to get a transparent material without cosmetic defects such as haze, due to poor solubility of filtering means, and the adaptation of the formulation of the optical material composition in order to solubilize the optical filtering means might modify the properties of the final optical material.

In view of the foregoing issues, there is a need for an optical material comprising a means capable of at least partially blocking transmission of UV and phototoxic blue light that is compatible with the other components of the optical material composition, without impairing the complete polymerization of optical material composition and mechanical properties of final optical material. It is also desirable that the optical material exhibits a low level of yellowness and no cosmetic defects. The optical material should be perceived as transparent and mostly colorless by an external observer.

The process for manufacturing such an article should be simple, easy to implement and reproducible. Another objective is to enhance productivity by shortening the preparation time of the optical material.

To address the needs of the present invention and to remedy to the mentioned drawbacks of the prior art, the applicant provides an optical material comprising a polymer matrix and at least one benzotriazole compound having at least one ester group, said at least one benzotriazole being a chlorobenzotriazole compound that does not comprise any polymerizable group selected from allylic, acrylic and methacrylic moieties, or optical transmittance through a 2 mm thick layer of said optical material being lower than 1% for each light wavelength ranging from 280 to 400 nm, and higher than 65% for light having a wavelength of 430 nm.

The invention provides a substrate-borne UV and blue light filter in a simple way and at competitive cost by using benzotriazole derivatives bearing an ester solubilizing group in order to achieve improved compatibility, which can be easily incorporated in polymerizable compositions in a very short processing time. The polymerizable compositions containing the UV-absorbers of the invention have good processability characteristics such as machinability, and are suitable as optical plastics.

Figure 2:
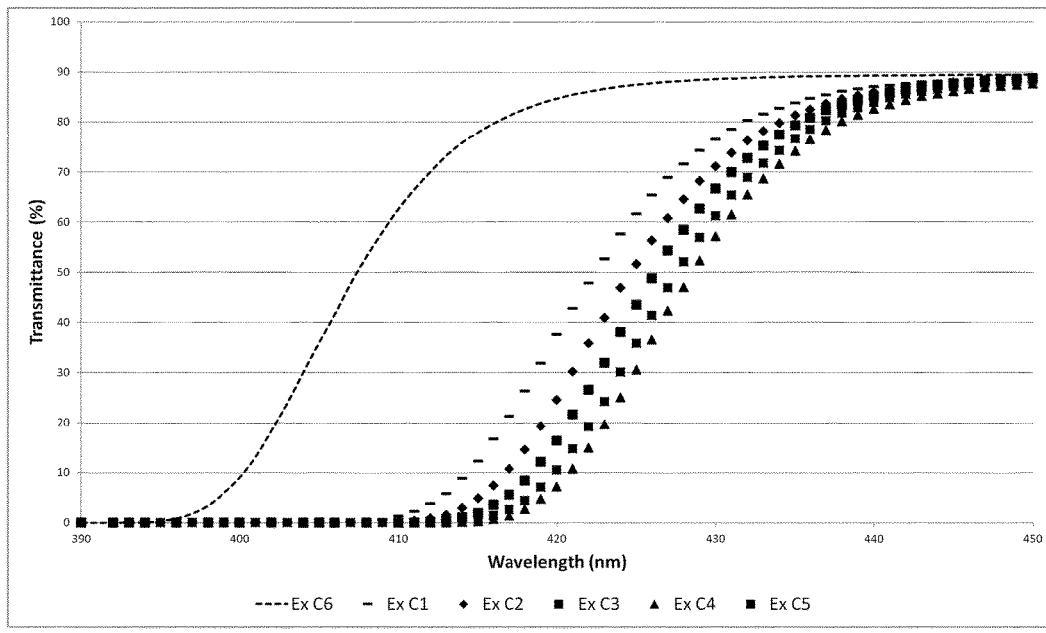

The foregoing and other objects, features and advantages of the present invention will become readily apparent to those skilled in the art from a reading of the detailed description hereafter when considered in conjunction with the accompanying drawing, wherein FIG. 1 represents the transmission spectrums between 390 and 450 nm of various optical materials according to the invention and FIG. 2 represents the transmission spectrums between 390 and 450 nm of comparative optical materials.

The optical material according to the invention is preferably used as the substrate of an optical article. It is generally comprised in a transparent optical article, in particular an optical lens or lens blank, more preferably an ophthalmic lens or lens blank.

In the present description, unless otherwise specified, an optical article/material is understood to be transparent when the observation of an image through said optical article is perceived with no significant loss of contrast, that is, when the formation of an image through said optical article is obtained without adversely affecting the quality of the image. This definition of the term "transparent" can be applied to all objects qualified as such in the description, unless otherwise specified.

In other embodiments, the optical material is used to form a coating, film or laminate useful e.g. in anti-reflective films or in liquid crystal display components. Optical materials are more particularly described hereunder in the context of a use as lens substrate, but are not limited to this use.

The term "ophthalmic lens" is used to mean a lens adapted to a spectacle frame to protect the eye and/or correct the sight. Said lens can be chosen from afocal, unifocal, bifocal, trifocal and progressive lenses. Although ophthalmic optics is a preferred field of the invention, it will be understood that this invention can be applied to optical elements of other types where filtering UV and blue wavelengths may be beneficial, such as, for example, lenses for optical instruments, filters particularly for photography or astronomy, optical sighting lenses, ocular visors, optics of lighting systems, screens, glazings, etc.

If the optical article is an optical lens, it may be coated on its front main surface, rear main side, or both sides with one or more functional coatings. As used herein, the rear face of the substrate is intended to mean the face which, when using the article, is the nearest from the wearer's eye. It is generally a concave face. On the contrary, the front face of the substrate is the face which, when using the article, is the most distant from the wearer's eye. It is generally a convex face. The optical article can also be a plano article.

A substrate, in the sense of the present invention, should be understood to mean an uncoated substrate, and generally has two main faces. The substrate may in particular be an optically transparent material having the shape of an optical article, for example an ophthalmic lens destined to be mounted in glasses. In this context, the term "substrate" is understood to mean the base constituent material of the optical lens and more particularly of the ophthalmic lens. This material acts as support for a stack of one or more coatings or layers.

The substrate of the article of the invention is an organic glass substrate, for instance an organic glass made from a thermoplastic or thermosetting plastic, generally chosen from transparent materials of ophthalmic grade used in the ophthalmic industry.

The benzotriazole UV absorbers of the present invention can be incorporated into any thermoplastic and thermoset resins, preferably thermoset resins.

Thermoplastic material may be selected from, for instance: polyamides; polyimide; polysulfones; polycarbonates; polyurethanes; poly(ethylene terephthalate), and polymethylmethacrylate (PMMA) and copolymers thereof. Preferred thermoplastic materials are polycarbonates.

The preferred class of substrate materials comprises thermoset resins which may be selected from, for instance: (meth)acrylic or thio(meth)acrylic polymers and copolymers or polyethoxylated aromatic (meth)acrylates, urethane and thiourethane polymers and copolymers, epoxy polymers and copolymers, episulfide polymers and copolymers, resins resulting from polymerization or (co)polymerization of alkylene glycol bis allyl carbonates such as polymers and copolymers of diethylene glycol bis(allylcarbonate) (marketed, for instance, under the trade name CR-39® by the PPG Industries company, the corresponding marketed lenses being referred to as ORMA® lenses from ESSILOR). The preferred substrates are made of thermoset materials, in particular resins resulting from polymerization or (co)polymerization of alkylene glycol bis allyl carbonates such as polymers and copolymers of diethylene glycol bis(allylcarbonate), polyurethane and polythiourethane resins, preferably polythiourethane resins, such as those having a refractive index of 1.60 or 1.67, or polyepisulfide resins, such as those having a refractive index of 1.74.

Specific examples of substrates suitable to the present invention are those obtained from thermosetting polythiourethane resins, which are marketed by the Mitsui Toatsu Chemicals company as MR® series, in particular MR6®, MR7® and MR8® resins. These substrates as well as the monomers used for their preparation are especially described in the U.S. Pat. Nos. 4,689,387, 4,775,733, 5,059,673, 5,087,758 and 5,191,055.

Other specific examples of substrates suitable for the present invention are those obtained from thermosetting resins comprising one monomer with epithio functions and one monomer with thiol function. Especially suitable monomers with epithio functions are linear aliphatic beta-epithiopropylthio compounds such as bis(2,3-epithiopropyl)sulfide, bis(2,3-epithiopropyl)disulfide, bis[4-(beta-epithiopropylthio)phenyl]sulfide, bis[4-(beta-epithiopropyloxy)cyclohexyl]sulfide. Especially suitable monomer with thiol function are aliphatic thiols such as 4-mercaptomethyl-1,8-dimercapto-3,6-dithiaoctane, 2,5-dimercaptomethyl-1,4-dithiane, 2,5-bis[(2-mercaptoethyl)thiomethyl]-1,4-dithiane, 4,8-dimercaptomethyl-1,11-dimercapto-3,6,9-trithiaundecane, 4,7-dimercaptomethyl-1,11-dimercapto-3,6,9-trithiaundecane and 5,7-dimercaptomethyl-1,11-dimercapto-3,6,9-trithiaundecane.

In particular, a thermosetting resin comprising bis(2,3-epithiopropyl)disulfide and a mixture of (4,8) or (4,7) or (5,7)-dimercaptomethyl-1,11-dimercapto-3,6,9-trithiaundecane is suitable for the invention and yields very efficient blue light blocking without increasing the level of yellowness of the substrate.

There are no particular restrictions on the method used to manufacture the optical article which includes a substrate made of an optical material according to the invention.

The polymer matrix of the present optical article can be obtained from methods that are well known to those of ordinary skill in the art, typically from an optical material composition ("substrate composition") comprising polymerizable compounds such as monomers, oligomers and/or prepolymers. The preferred polymerizable compounds are allyl glycol carbonates, polythiols, episulfides, polyisocyanates, polyisothiocyanates and (meth)acrylates. The preferred combinations of polymerizable compounds are a combination of diethylene glycol bis(allylcarbonate) and eventually oligomers of diethylene glycol bis(allylcarbonate), a combination of a polyisocyanate compound and a polyol compound, a combination of a polyisocyanate compound and a polythiol compound, and a combination of a polyepisulfide compound and a polythiol compound. Examples of useful polymerizable compounds are disclosed e.g. in WO 2014/133111.

The benzotriazole compounds of the present invention can be incorporated into the mass of the substrate by methods well known in the art, preferably during the manufacture of the substrate itself, for example by casting polymerization or injection molding.

This is preferably carried out by mixing the compound in the optical material composition (an optical material resin or a polymerizable composition) and then forming the substrate by curing the (liquid) composition in an appropriate mold.

More specifically, the optical material composition is poured into the cavity of a mold held together using a gasket or tape. Depending on the desired characteristics of the resulting optical material, degassing can be performed under reduced pressure and/or filtration can be performed under increased pressure or reduced pressure before pouring the optical material composition in the mold. After pouring the composition, the casting mold, preferably a lens casting mold, can be heated in an oven or a heating device immersed in water according to a predetermined temperature program to cure the resin in the mold. The resin molded product may be annealed if necessary.

Other methods can also be employed, in particular when the benzotriazole compound is not sufficiently resistant to the high temperatures involved during casting or injection molding. Such methods include impregnation or imbibition methods consisting in dipping the substrate in an organic solvent and/or water based hot bath in which the benzotriazole has been dispersed (which then diffuses in the body of the substrate), the diffusion methods described in JP 2000-314088 and JP 2000-241601, involving an impregnable temporary coating, or contactless coloration using a sublimable material, such as described in U.S. Pat. Nos. 6,534,443 and 6,554,873.

The optical material composition can contain additives commonly used in the art other than those mentioned above, for example internal mold release agents, resin modifiers, light stabilizers, polymerization catalysts, color balancing agents, chain extenders, crosslinking agents, free radical scavengers such as antioxidants, dyes, pigments, fillers, and adhesion accelerators.

The optical material composition according to the invention generally comprises a system for initiating the polymerization (catalyst). The polymerization initiating system can comprise one or more thermal or photochemical polymerization initiating agents or alternatively, a mixture of thermal and photochemical polymerization initiating agents, depending on the nature of the polymerizable compounds. Generally, the initiating agents are used in a proportion of 0.01 to 5% by weight with respect to the total weight of polymerizable compounds present in the composition.

In particular, for substrates resulting from polymerization or (co)polymerization of polyurethane and polythiourethane resins, preferred catalysts are selected from alkyltins, alkyltin oxides, metal coordination complexes or amines, more preferably alkyltins. A preferred proportion for alkyltins is 0.02 to 2% by weight with respect to the total weight of polymerizable compounds present in the composition. Preferred alkyltins are dibutyltin dichloride and dimethyltin dichloride.

Generally, blocking visible wavelengths such as undesirable blue light affects color balance, color vision if one looks through the optical device, and the color in which the optical device is perceived. Indeed, light-blocking optical devices incorporating at least one of the above described benzotriazoles that at least partially inhibits visible light tend to produce a color tint in the optical article as a "side effect", the latter appearing yellow, brown or amber. This is esthetically unacceptable for many optical applications, and may interfere with the normal color perception of the user if the device is an ophthalmic lens.

In order to compensate for the yellowing effect of the blue light blocking benzotriazole and obtaining an optical article having a cosmetically acceptable appearance for the wearer and when viewed by an external observer, in particular perceived as mostly color neutral, the optical article comprises, in one embodiment, at least one color-balancing component, when obtaining a colorless appearance is desired.

The color balancing component can be incorporated into the substrate of the optical article using the same methods are those previously described for the incoporation of the benzotriazole compounds, or in at least one coating/film applied on the surface of the substrate, such as a primer coating or hard coat. It is preferably incorporated into the optical material itself, i.e., in the optical material composition used to prepare the optical material, preferably by casting or injection molding.

In the present invention, the color balancing agent is preferably a bluing agent, i.e., a compound having an absorption band in the visible light spectrum in the orange to yellow wavelength region and manifesting a color from blue to violet.

In one embodiment, the color-balancing component employed to at least partially offset the yellowing effect is a dye or a pigment, such as a blue tinting dye, or a mixture of dyes used in suitable proportions, such as a combination of red and green tinting dyes.

Examples of suitable fixed-tint colorants can include any of the art recognized inorganic and organic pigments and/or dyes. Inorganic dyes and pigments can be selected from ultramarine blue, iron blue (Prussian blue—potassium ferric ferrocyanide), and cobalt blue. Organic dyes and pigments can be selected from azo dyes (monoazo and diazo compounds), polymethyne dyes, arylmethyne dyes, polyene dyes, anthracenedione dyes, pyrazolone dyes, quinophtalone dyes and carbonyl dyes. Specific examples of such organic dyes include Blue 6G, Violet PF and Magenta RB available from Keystone Aniline, Morplas Blue from Morton International, Inc., D&C Violet #2 available from Sensient Corp., Macrolex Violet 3R from Bayer, Diaresin Blue J supplied by Mitsubishi Chemical Corporation, and Rubine Red from Clariant Corporation. Also suitable are laser dyes, for example those selected from pyrromethene, fluoroscein, rhodamine, malachit green, azine compounds such as oxazine or carbazine, triallylmethane compounds, condensed polycyclic compounds (e.g. indigo compounds and anthraquinone compounds), pyridines, carbocyanine iodide, phthalocyanine compounds and others. Specific examples include ABS 574, ABS 668 or ABS 674 from Exiton, Inc.; or SDA2443, SDA3572 or ADA4863 available from H. W. Sands Corp. Mixtures of any of the aforementioned dyes can be used.

In another embodiment, the color balancing component is an optical brightener, also called fluorescent whitening agent (FWA), optical brightening agent (OBA) or fluorescent brightening agent (FBA). As well known, optical brighteners are substances that absorb light in the UV and violet region (usually at 340-370 nm) and emit light by fluorescence mainly in the blue region of the visible spectrum (400-500 nm) in order to mask the yellow color imparted by the benzotriazoles. Preferred optical brighteners have high fluorescence efficiency, i.e., re-emit as visible light a major proportion of the energy they have absorbed.

The optical brightener may be chosen, without limitation to these families, from stilbenes, carbostyrils, coumarins, 1,3-diphenyl-2-pyrazolines, naphthalimides, combined heteroaromatics (such as pyrenyl-triazines or other combinations of heterocyclic compounds such as thiazoles, pyrazoles, oxadiazoles, fused polyaromatic systems or triazines, directly connected to each other or through a conjugated ring system) benzoxazoles, in particular benzoxazoles substituted at the 2-position with a conjugated ring system, preferably comprising ethylene, phenylethylene, stilbene, benzoxazole and/or thiophene groups. Preferred families of optical brighteners are bis-benzoxazoles, phenylcoumarins, methylcoumarins and bis-(styryl)biphenyls, which are described in more details in A. G. Oertli, Plastics Additives Handbook, 6th Edition, H. Zweifel, D. Maier, M. Schiller Editors, 2009. The most preferred optical brighteners are 2,2'-(1,2-ethylenediyldi-4,1-phenylene) bisbenzoxazole, marketed by Eastman Chemical under the trade name Eastobrite® OB-1 and 2,5-thiophenediylbis(5-tert-butyl-1,3-benzoxazole), marketed by BASF under the tradename Tinopal® OB.

The color balancing component is generally used in an amount sufficient to adjust the hue of the optical material, typically from 0.01 to 5% by weight, more preferably from 0.1 to 2%, relative to the weight of the optical material composition (or per 100 parts by weight of the polymerizable compounds or relative to the material total weight). This amount depends on the nature (strength) and the amount of the benzotriazole that is used, and on the final color and transmission desired. Those of skill in the art should appreciate that the respective amounts of color-balancing component and benzotriazole have to be adapted to each other to produce a transparent, colorless material. To this end, the optimal amounts of each compound can be determined by simple laboratory experiments.

The benzotriazoles according to the invention are benzotriazoles having at least one ester group acting as a solubilizing chain that makes easier the preparation of a homogeneous optical material composition. As compared to previously known benzotriazole UV absorbers, benzotriazoles according to the invention allow to significantly reduce the manufacturing time of the optical materials, while maintaining high optical properties such as a high blue light cut level.

The first family of benzotriazoles according to the invention comprises chlorobenzotriazoles having at least one ester group and no polymerizable group selected from allylic, acrylic and methacrylic moieties. The benzotriazoles according to the invention do preferably not comprise any unsaturated polymerizable group or cross-linking group, such as a non aromatic C=C double bond, which could reticulate the benzotriazole within the substrate during polymerization.

The second family of benzotriazoles according to the invention comprises benzotriazoles having at least one ester group and that lead to an optical material having an optical transmittance lower than 1% for each light wavelength ranging from 280 to 400 nm, preferably from 280 to 405 nm, and higher than 65% for light having a wavelength of 430 nm, when incorporated into a 2-mm thick layer of said material. The benzotriazoles of the second family according to the invention do preferably not comprise any resonant group on the benzotriazole ring, in particular no halogen atom and especially no chlorine atom. Preferably, the benzotriazoles of the second family according to the invention lead to an optical material having an optical transmittance higher than 75% for light having a wavelength of 430 nm The benzotriazole having at least one ester group is preferably a 1-arylbenzotriazole or a 2-arylbenzotriazole, more preferably a 2-arylbenzotriazole, still more preferably a compound of formula (I) defined as not comprising any polymerizable group selected from allylic, acrylic and methacrylic moieties, more preferably that does not comprise any unsaturated polymerizable group or cross-linking group, such as a non aromatic C=C double bond:

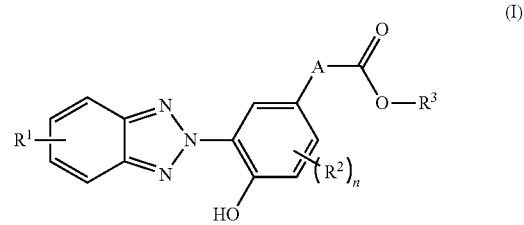

(I)

in which A is a divalent group, R' is a resonant group or a hydrogen atom, the $R^2$ groups are identical or different monovalent groups, n is an integer ranging from 1 to 3, and $R^3$ is a linear or branched, substituted or unsubstituted alkyl or aryl group.

In the present patent application, the term "alkyl" means a linear or branched, saturated or unsaturated monovalent hydrocarbon-based radical, preferably containing from 1 to 25 carbon atoms. The term alkyl includes acyclic groups preferably containing from 1 to 8 carbon atoms such as methyl, ethyl, n-propyl, isopropyl, butyl and n-hexyl groups, the cycloalkyl groups preferably containing from 3 to 7 carbon atoms, the cycloalkylmethyl groups preferably containing from 4 to 8 carbon atoms.

The term "cycloalkyl" also includes "heterocycloalkyl" groups, i.e. non-aromatic monocyclic or polycyclic rings in which one or more carbon atoms of the ring(s) have been replaced with a heteroatom such as nitrogen, oxygen, phosphorus or sulfur. The heterocycloalkyl group preferably comprises 1 to 4 endocyclic heteroatoms. The heterocycloalkyl groups may be structures containing one or more nonaromatic rings. In the structures bearing several rings, the rings may be fused, covalently linked or linked via a common divalent group such as a methylene, ethylene or carbonyl group. A heterocycloalkyl group can have one or more carbon-carbon double bonds or carbon-heteroatoms double bonds in the ring as long as the ring is not rendered aromatic by their presence. Preferably, the heterocycloalkyl group is a monocyclic or bicyclic ring, more preferably, a monocyclic ring, wherein the ring comprises from 2 to 6 carbon atoms and from 1 to 3 heteroatoms. Illustrative examples of heterocycloalkyl groups include, but are not limited to, aziridinyl, pyrrolidinyl, piperidinyl, piperazinyl, morpholinyl, thiomorpholinyl, thiomorpholino, tetrahydrofuranyl, tetrahydrothiofuranyl, tetrahydropyranyl, and pyranyl.

The term "substituted alkyl" group means an alkyl group as defined above, connected via an $sp^3$ carbon atom and substituted with one or more aryl groups and/or comprising one or more heteroatoms such as N, S or O. Examples that can be mentioned include arylalkyl groups such as the trityl group (—$CPh_3$), the benzyl group or the 4-methoxybenzyl group, alkoxyalkyl groups, especially dialkoxymethyl groups such as diethoxymethyl or dimethoxymethyl groups, $CH_2CO_2R^{11}$ groups, in which $R^{11}$ represents an optionally substituted alkyl or aryl group.

The terms "alkylene" and "substituted alkylene" correspond to the divalent version of the alkyl and substituted alkyl groups as defined above.

The term "ester group" denotes a group of formula —$C(O)OR^{10}$, $R^{10}$ denoting an optionally substituted aryl or alkyl group.

The term "aryl" denotes an aromatic monovalent carbocyclic radical comprising only one ring (for example a phenyl group) or several, optionally fused, rings (for example naphthyl or terphenyl groups), which may optionally be substituted with one or more groups such as, without limitation, alkyl (for example methyl), hydroxyalkyl, aminoalkyl, hydroxyl, thiol, amino, halo (fluoro, bromo, iodo or chloro), nitro, alkylthio, alkoxy (for example methoxy), aryloxy, monoalkylamino, dialkylamino, acyl, carboxyl, alkoxycarbonyl, aryloxycarbonyl, hydroxysulfonyl, alkoxysulfonyl, aryloxysulfonyl, alkylsulfonyl, alkylsulfinyl, cyano, trifluoromethyl, tetrazolyl, carbamoyl, alkylcarbamoyl or dialkylcarbamoyl groups. Alternatively, two adjacent positions of the aromatic ring may be substituted with a methylenedioxy or ethylenedioxy group.

The term "aryl" also includes "heteroaryl" groups, i.e. aromatic rings in which one or more carbon atoms of the aromatic ring(s) have been replaced with a heteroatom such as nitrogen, oxygen, phosphorus or sulfur. The heteroaryl group preferably comprises 1 to 4 endocyclic heteroatoms. The heteroaryl groups may be structures containing one or more aromatic rings, or structures containing one or more aromatic rings coupled with one or more nonaromatic rings. In the structures bearing several rings, the rings may be fused, covalently linked or linked via a common divalent group such as a methylene, ethylene or carbonyl group.

Examples of heteroaryl groups are thienyl (2-thienyl, 3-thienyl), pyridyl (2-pyridyl, 3-pyridyl, 4-pyridyl), isoxazolyl, oxazolyl, phthalimidyl, pyrazolyl, indolyl, furanyl, quinolinyl, phenothiazinyl, thiazolyl, (1,2,3)- and (1,2,4)-triazolyl, tetrazolyl, carbazolyl, pyrazinyl, pyridazinyl, pyrimidyl, triazinyl, pyrrolyl, imidazolyl, benzopyranonyl, and benzofused analogs thereof. Preferably, a heteroaryl group is a monocyclic ring, wherein the ring comprises 2 to 5 carbon atoms and 1 to 3 heteroatoms.

$R^1$ is H or a resonant group, i.e., a group providing resonance to the structure, which is preferably selected from halogen, cyano, amino, hydroxyl, mercapto, carboxy, alkoxy, aryloxy, alkylsulfanyl and arylsulfanyl. In one embodiment, $R^1$ is H or a halogen atom.

The best $R^1$ groups are electron donating groups because they have the ability of shifting to the red end the benzotriazole absorption spectrum, i.e., to the high wavelengths. However, electron withdrawing groups are also suitable to shift to the red end the benzotriazole absorption spectrum, if they are able to bring a resonance effect. This red shifting effect results in an optical material having a more significant extinction in the blue-violet region of the visible spectrum (400-450 nm), in other words a higher light cut-off wavelength.

The $R^1$ group is preferably a halogen atom in position 4 or 5 on the benzotriazole group. The preferred $R^1$ group is a chloro group, which is ideally located in position 4 or 5 on the aryl group. The most preferred position for $R^1$ group is position 5 on the benzotriazole group.

The A group is a divalent group, for example an optionally substituted, linear or branched alkylene group (the preferred substituents being linear or branched alkyl groups, or aryl groups), an optionally substituted cycloalkylene group, an optionally substituted arylene group, or a combination of the previously mentioned groups of the same category and/or of various categories, especially cycloalkylenealkylene, biscycloalkylene, biscycloalkylenealkylene, arylenealkylene, bisphenylene and bisphenylenealkylene groups. Preferred alkylene groups include linear C1-C10 alkylene groups, for example a methylene group —$CH_2$—, an ethylene group —$CH_2$—$CH_2$—, a butylene or a hexylene, especially 1,4-butylene and 1,6-hexylene and branched C3-C10 alkylene radicals such as 1,4-(4-methyl pentylene), 1,6-(2,2,4-trimethyl hexylene), 1,5-(5-methyl hexylene), 1,6-(6-methyl heptylene), 1,5-(2,2,5-trimethyl hexylene), 1,7-(3,7-dimethyl octylene), 2,2-(dimethylpropylene), 1,1-dimethylpentylene (with the quaternary carbon atom connected to the aryl group in formula I) and 1,6-(2,4,4-trimethyl hexylene) radicals. Preferred cycloalkylene radicals include cyclopentylene and cyclohexylene radicals, optionally substituted especially by alkyl groups.

In one embodiment, A represents a —($CR^5R^6$)— group, in which $R^5$ and $R^6$ represent independently H or alkyl groups, preferably C1-C6 linear or branched alkyl groups, optionally substituted with groups such as aryl groups. This group is preferably a —($CHR^5$)— group ($R^6$=H).

In another embodiment, A represents a —($CR^5R^6$—$CR'^5R'^6$)— group, in which $R^5$, $R'^5$, $R^6$ and $R'^6$ represent independently H or alkyl groups, preferably C1-C6 linear or branched alkyl groups, optionally substituted with groups such as aryl groups. This group is preferably a —($CHR^5$—$CHR'^5$)— group ($R^6$=$R'^6$=H).

The A group is preferably a substituted or unsubstituted linear or branched alkylene group comprising from 1 to 6 carbon atoms. A is preferably a linear group, such as the methylene, ethylene, 1,3-propylene, 1,4-butylene, 1,5-pentylene and 1,6-hexylene groups. The preferred A group is the ethylene group, giving rise to propionate esters.

The $R^2$ groups are identical or different monovalent groups, which are preferably selected from a hydrogen atom, saturated or unsaturated, linear or branched, substituted or unsubstituted hydrocarbon (such as alkyl) groups comprising from 1 to 12 carbon atoms, preferably from 2 to 10 carbon atoms, still preferably from 2 to 5 carbon atoms (hydrocarbon groups are connected to the aryl group through a carbon atom), for example arylalkyl groups, and groups such as hydroxyalkyl, aminoalkyl, hydroxyl, thiol, amino, halo (fluoro, bromo, iodo or chloro), nitro, alkylthio, alkoxy, aryloxy, monoalkylamino, dialkylamino, acyl, carboxyl, alkoxycarbonyl, aryloxycarbonyl, hydroxysulfonyl, alkoxysulfonyl, aryloxysulfonyl, alkylsulfonyl, alkylsulfinyl, cyano, trifluoromethyl, tetrazolyl, carbamoyl, alkylcarbamoyl or dialkylcarbamoyl groups. The $R^2$ groups are preferably identical or different groups chosen from a hydrogen atom and linear or branched, substituted or unsubstituted hydrocarbon groups comprising from 1 to 6 carbon atoms.

n is preferably equal to 1.

The compound of formula I preferably comprises a (single) $R^2$ group in position 3 on the aryl group, i.e., in ortho position relative to the hydroxyl group. $R^2$ is preferably a sterically hindered alkyl group, such as a 1,1-dimethylpentyl group, an isopropyl group or a t-butyl group, preferably a t-butyl group.

$R^3$ is a linear or branched, substituted or unsubstituted alkyl or aryl group, preferably a linear or branched, substituted or unsubstituted alkyl group comprising from 1 to 14 carbon atoms, more preferably from 2 to 10 carbon atoms, still more preferably from 4 to 9 carbon atoms. $R^3$ is preferably a C7-C9 linear or branched alkyl group, such as a n-octyl group or an ethylhexyl group. In some embodiments, mixture of compounds of formula (I) having identical substituents but different $R^3$ groups are used, such as isomeric $R^3$ groups (having the same number of carbon atoms and a different spatial arrangement), or a mixture of linear or branched C7-C9 alkyl chains.

In one embodiment, $R^3$ is a cycloalkyl or heterocycloalkyl group having a C5-C7 ring optionally substituted with identical or different groups that may be selected from the same groups as the $R^2$ groups, preferably linear or branched alkyl chains comprising from 1 to 6 carbon atoms, linear or branched alkoxy chains comprising from 1 to 6 carbon, hydroxyl groups, and amino groups.

The preferred compounds of formula I are those wherein n=1, $R^2$ is a linear or branched alkyl group comprising from 1 to 6 carbon atoms, $R^3$ is a linear or branched alkyl group comprising from 1 to 10 carbon atoms, and A is a linear alkylene group comprising from 1 to 4 carbon atoms. Among those compounds, those of formula (Ia) are preferred

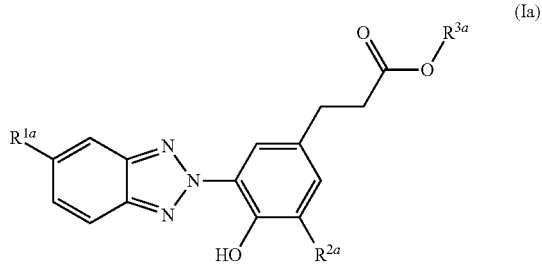
(Ia)

In this formula, $R^{1a}$ is H or a halogen atom, $R^{2a}$ is a linear or branched alkyl group comprising from 1 to 6 carbon atoms and $R^{3a}$ is a linear or branched alkyl group comprising from 5 to 10 carbon atoms.

Specific examples of benzotriazole esters according to the invention are n-octyl-3-[3-tert-butyl-4-hydroxy-5-(5-chloro-2H-benzotriazol-2-yl)phenyl] propionate of formula (IV) and octyl-3-[3-tert-butyl-4-hydroxy-5-(2H-benzotriazol-2-yl)-phenyl] propionate in which the octyl moiety is a mixture of branched and linear alkyls, of formula (V):

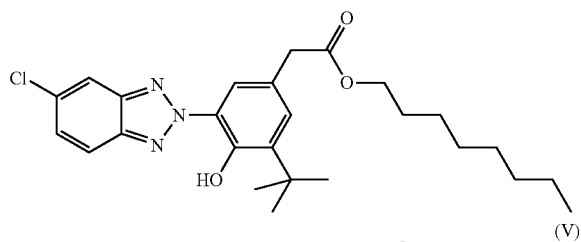
(IV)

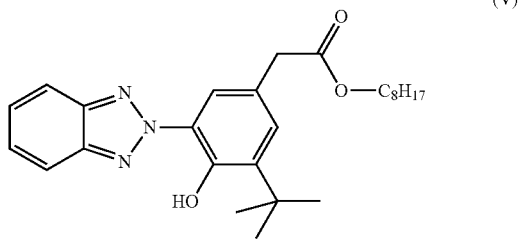
(V)

The amount of benzotriazole compounds used in the present invention is an amount sufficient to provide a satisfactory protection from blue light and UV light but not excessive so as to prevent precipitation. The inventive benzotriazole compounds are generally present in an amount ranging from 0.1 to 5% by weight relative to the optical material total weight (or per 100 parts by weight of the polymerizable compounds or relative to the weight of the optical material composition), preferably from 0.2 to 3% by weight, more preferably from 0.5 to 2.5% by weight.

The benzotriazole UV absorbers that may be used in the present invention have the ability to at least partially block light having a wavelength shorter than 400 nm, but also have an absorption spectrum extending to visible blue light range of the electromagnetic spectrum (400-500 nm).

Thus, the benzotriazole ester compounds of the invention, and particularly the chlorobenzotriazole esters, are efficient to improve blue light cutting by absorption, even when used in small amounts. The resulting optical material thus provides a high level of retinal cell protection against retinal cell apoptosis or age-related macular degeneration.

The optical material according to the invention preferably blocks or cuts at least 80% of the light having a wavelength ranging from 280 to 380 nm (preferably from 280 to 400 nm, still more preferably from 280 to 405 nm), more preferably at least 90% and still more preferably at least 95%, essentially though absorption by the benzotriazole UV absorber. In most preferred embodiments, at least 96%, 97%, 98%, 99%, 99.5% or 99.9% of light in the 280-380 nm or 280-400 nm ranges is blocked.

In the present application, "blocking X %" of incident light in a specified wavelength range does not necessarily mean that some wavelengths within the range are totally blocked, although this is possible. Rather, "blocking X %"

of incident light in a specified wavelength range means that an average of X % of said light within the range is not transmitted.

In addition, light blocking is considered here for an optical material devoid of any coating, especially antireflective coating. It means that light reflected by optical material is not transmitted and considered as blocked.

The light cut-off wavelength of the optical material is preferably higher than or equal to 400 nm, more preferably higher than or equal to 405 nm, and even more preferably higher than or equal to 410 nm. It is preferably lower than 465 nm, more preferably lower than 450 nm. In the present disclosure, the light cut-off wavelength is defined as the wavelength below which light transmission becomes lower than 1%. In other words, it is the highest wavelength for which the transmittance is lower than 1%. The higher the light cut-off wavelength, the better the blue light cutting properties.

In the present description, unless otherwise specified, optical transmittances/transmissions are measured at the center of the optical article for a thickness ranging from 0.7 to 2 mm, preferably 2 mm, at normal incidence. As used herein, optical transmittance within a wavelength range is an average of light transmitted within this range and is not weighted according to the sensitivity of the eye at each wavelength of the range, unless otherwise specified. Last, optical transmittance is measured for optical articles having no coatings, in particular no antireflective coatings. In particular, reflection at both air/substrate interfaces reduces significantly optical transmittance, around 4-5% for each interface, i.e. 8-10% for a lens.

In one embodiment, the optical material is configured such that the optical transmittance of the optical article is satisfying at least one of the characteristics (1) to (3) below and preferably these three characteristics:

(1) the optical transmittance at 400 nm is 1% or less;
(2) the optical transmittance at 420 nm is 60% or less;
(3) the optical transmittance at 440 nm is 80% or more.

Further, it may be particularly desirable in some cases to selectively filter a relatively small portion of the blue spectrum, i.e., within the 380-450 nm region. Indeed, it has been found that blocking too much of the blue spectrum can interfere with scotopic vision and mechanisms for regulating biorhythms, referred to as "circadian cycles". Thus, in a preferred embodiment, the optical material blocks less than 1% of light having a wavelength ranging from 465 to 495 nm, preferably from 450 to 550 nm. In this embodiment, the optical material selectively blocks the phototoxic blue light and transmits the blue light implicated in circadian rhythms. Preferably, the optical material transmits at least 85% of light having a wavelength ranging from 465 to 495 nm, more preferably from 450 to 550 nm. In another embodiment, the optical material does not absorb light in the 465-495 nm range, preferably the 450-550 nm range.

The optical material according to the invention and preferably have a relative light transmission factor in the visible spectrum Tv higher than or equal to 85%, preferably higher than or equal to 87%, more preferably higher than or equal to 88%, and better higher than or equal to 89%.

Optical articles made from optical material according to the invention can be coated with antireflective coatings on one or both air/substrate interface(s). In such embodiments, Tv factor preferably ranges from 85% to 99%, more preferably from 88% to 98%, even better from 88% to 97%.

The Tv factor, also called "luminous transmission" of the system, is such as defined in the standard NF EN 1836 and relates to an average in the 380-780 nm wavelength range that is weighted according to the sensitivity of the eye at each wavelength of the range and measured under D65 illumination conditions (daylight).

The optical material according to the invention has improved color properties, especially when it is color-balanced, which can be quantified by the yellowness index Yi. The degree of whiteness of the inventive optical material may be quantified by means of colorimetric measurements, based on the CIE tristimulus values X, Y, Z such as described in the standard ASTM E313 with illuminant C observer 2°. The optical material according to the invention preferably has a low yellowness index Yi, i.e., lower than 10, more preferably lower than 5, as measured according to the above standard. The yellowness index Yi is calculated per ASTM method E313 through the relation $Yi=(127.69\,X-105.92\,Z))/Y$, where X, Y, and Z are the CIE tristimulus values.

Another advantage of the present benzotriazole compounds is that, as ester derivatives, they are in oily form, which enables an easy and rapid dissolution in the optical material composition without having to screen raw materials such as disclosed in the patent JP 4206820 that mentions a specific benzotriazole diameter size of less than 500 μm to facilitate dissolution.

A further advantage of the ultraviolet-absorbing benzotriazole compound bearing an ester group used herein is that they are compatible with the polymerizable composition and the resulting polymerized material even though the molecular weights or the species that are present is "high". No precipitation is observed after curing, even at high concentration, while the patent JP 4206820 teaches the use of benzotriazoles with a molecular weight of less than 360 g/mol in order to provide compatibility with the material formulation compounds.

The invention also relates to a method for preparing an optical material such as herein described, comprising:
obtaining a polymerizable composition comprising at least one ultraviolet-absorbing benzotriazole compound having at least one ester group as described previously, and at least one polymerizable compound,
curing said polymerizable composition, preferably in a mold, so as to form the optical material comprising a polymer matrix and said at least one benzotriazole compound having at least one ester group.

In a preferred embodiment, a homogeneous polymerizable composition is obtained at room temperature (25° C.) in less than 20 minutes, more preferably less than 15 minutes, still more preferably less than or equal to 10 minutes.

In another preferred embodiment, said at least one polymerizable compound is selected from allyl glycol carbonates, polythiols, episulfides, polyisocyanates, polyisothiocyanates and (meth)acrylates.

In one embodiment of the invention, the polymerizable composition is prepared by first mixing the benzotriazole comprising at least one ester bond with at least one first monomer to obtain a homogeneous first composition, and then at least one second monomer is optionally added in said composition to obtain a second composition. Additives such as catalysts can be added to the first and/or second composition. In some aspects of the invention, homogeneity of said first composition is obtained in less than 20 minutes, more preferably less than 15 minutes, still more preferably less than or equal to 10 minutes.

The process according to the invention in advantageous since it requires no specific steps such as tinting and no specific coating comprising UV absorbers.

The invention further relates to a plastic eyeglasses lens comprising a lens substrate, the lens substrate being obtained from the above disclosed optical material, preferably by molding.

The following examples illustrate the present invention in a more detailed, but non-limiting manner. Unless stated otherwise, all thicknesses disclosed in the present application relate to physical thicknesses.

EXAMPLES

1. Chemicals Used

Optical materials were prepared from a composition comprising polymerizable monomers, at least one benzotriazole compound (UV absorber), dimethyltin dichloride as a catalyst (CAS No. 753-73-1) and Diaresin blue J as a bluing agent (CAS No. 86090-40-6).

The monomers used in the present examples were the bisisocyanatonorbonane (ISO, CAS No. 74091-64-8), the pentaerythritol tetrakis (3-mercaptopropionate) (THIOL1, CAS No. 7575-23-7), and 2,3-bis((2-mercaptoethyl)thio)-1-propanethiol (THIOL2, CAS No. 131538-00-6), in order to produce a polythiourethane matrix.

The benzotriazole UV absorbers according to the invention used in the examples were Eversorb® 109 (n-octyl-3-[3-tert-butyl-4-hydroxy-5-(5-chloro-2H-benzotriazol-2-yl)phenyl] propionate, CAS No. 83044-89-7, formula IV) and Eversorb® 82 (octyl-3-[3-tert-butyl-4-hydroxy-5-(2H-benzotriazol-2-yl)-phenyl] propionate branched and linear alkyl esters, CAS No. 127519-17-9, formula V). Eversorb® 82 of formula V is a compound leading to an optical material having an optical transmittance lower than 1% for each light wavelength ranging from 280 to 400 nm, and higher than 65% for light having a wavelength of 430 nm (for a 2-mm thick layer of material). The structures of these compounds are reminded hereunder:

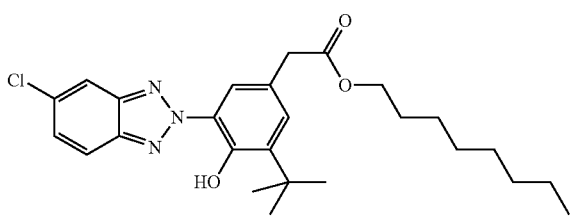

(IV)

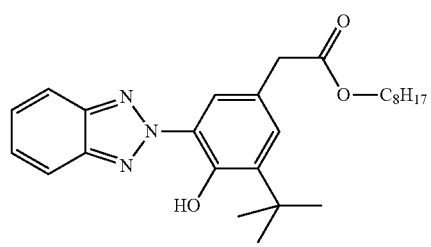

(V)

The following comparative benzotriazole UV absorbers, devoid of ester group, were also used: Seesorb® 709 (2-(2-hydroxy-5-tert-octylphenyl)benzotriazole, CAS No. 3147-75-9, formula VI) and Seesorb® 703 (2-(2-hydroxy-3-tert-butyl-5-methylphenyl)-5-chlorobenzotriazole, CAS No. 3896-11-5, formula VII). The structures of these compounds are reminded hereunder:

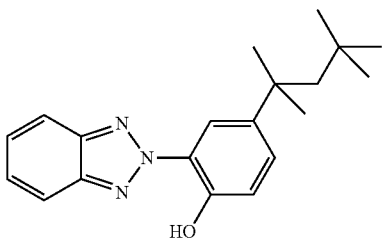

(VI)

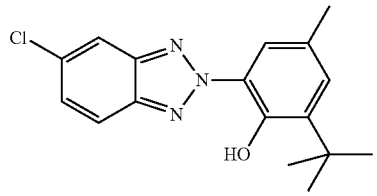

(VII)

2. Manufacture of Lenses by Casting

Convex and concave molds were assembled by using typing process. A center thickness adjustment was made to obtain 2 mm thick samples.

The formulations of examples 1-5 and C1-06 were prepared in small batch size by using a 100 mL Duran bottle with a glass tube for nitrogen intake and a vacuum connection. The benzotriazole UV absorber component was mixed with the ISO monomer (isocyanate part) at room temperature (25° C.) until a homogeneous mixture was obtained or, if the benzotriazole UV absorber was not dissolved at room temperature (25° C.), under moderate heat (30° C., comparative examples C4 and C5 only). Solubilization speed was recorded and is shown in the tables hereunder.

The dimethyl tin dichloride catalyst was added in the reaction mixture, which was then cooled down to 10° C. prior to addition of the thiol monomers THIOL1 and THIOL2, and stirred under vacuum until homogeneous. The bluing agent was added at the end of the preparation. The appearance of the final formulations was checked at this time and is shown in the tables hereunder.

The assembled molds were filled with the final formulations using a syringe, and the polymerization reaction was carried out in a regulated electronic oven at maximum 130° C. for 1 day. The molds were then disassembled to obtain lenses comprising a body of a thermoset material. The lenses were cleaned by immersion and sonication in a surfactant solution, then rinsed and dried. Their appearance was checked at this time and is shown in the tables hereunder.

3. Formulations Prepared and Characterizations

The formulations prepared and the characterizations of these formulations and the final lenses are shown in the tables hereunder.

The light transmission factor in the visible spectrum Tv was measured in transmission mode from a wearer's view angle using a Cary 4000 spectrophotometer from Hunter, with the back (concave) side of the lens (2 mm thickness at the center) facing the detector and light incoming on the front side of the lens. Tv was measured under D65 illumination conditions (daylight).

The yellowness index YI of the prepared lenses was calculated as described above, by measuring on a white background with the above spectrophotometer the CIE tristimulus values X, Y, Z such as described in the standard ASTM E 313-05, through reflection measures, with the front (convex) side of the lens facing the detector and light incoming on said front side. This way of measuring YI, from an observer's view angle, is the closest to the actual wearing situation.

The light cut-off wavelength was determined from the transmission spectra, which are shown on FIGS. 1 and 2. Transmission values for wavelengths lower than 390 nm (not shown on figures) were lower than 0.1%, for inventive and comparative examples.

| Compound | Examples | | | | |
|---|---|---|---|---|---|
| (parts by weight) | 1 | 2 | 3 | 4 | 5 |
| Benzotriazole IV | 1.25 | 1.50 | 2.00 | 1.25 | |
| Benzotriazole V | | | | | 1.25 |
| ISO | 50.60 | 50.60 | 50.60 | 50.60 | 50.60 |
| THIOL1 | 23.90 | 23.90 | 23.90 | 23.90 | 23.90 |
| THIOL2 | 25.29 | 25.29 | 25.29 | 24.00 | 25.29 |
| Catalyst | 0.04 | 0.04 | 0.04 | 0.04 | 0.04 |
| Bluing agent | 0.21 | 0.21 | 0.21 | 1.50 | 0.21 |
| Total | 101.29 | 101.54 | 102.04 | 101.29 | 101.29 |
| Solubilization speed (min) | 4 | 4 | 5 | 4 | 5 |
| Final formulation appearance | o | o | o | o | o |
| Lens appearance | o | o | o | o | o |
| Tv (%) | 89.3 | 89.1 | 89.1 | 87.6 | 89.3 |
| T (%) at 430 nm | 80 | 78 | 75 | 79 | 87 |
| Light cut-off (nm) | 409 | 410 | 412 | 409 | 400 |
| YI | 6.2 | 6.9 | 7.8 | 4.6 | 2.5 |

| Compound (parts by weight) | Comparative examples | | | | | |
|---|---|---|---|---|---|---|
| | C1 | C2 | C3 | C4 | C5 | C6 |
| Benzotriazole VII | 0.50 | 0.75 | 1.00 | 1.25 | 1.50 | 0.01 |
| Benzotriazole VI | | | | | | 1.20 |
| ISO | 50.60 | 50.60 | 50.60 | 50.60 | 50.60 | 50.60 |
| THIOL1 | 23.90 | 23.90 | 23.90 | 23.90 | 23.90 | 23.90 |
| THIOL2 | 25.29 | 25.29 | 25.29 | 25.29 | 25.29 | 25.50 |
| Catalyst | 0.04 | 0.04 | 0.04 | 0.04 | 0.04 | 0.04 |
| Bluing agent | 0.21 | 0.21 | 0.21 | 0.21 | 0.21 | 0.21 |
| Total | 100.54 | 100.79 | 101.04 | 101.29 | 101.54 | 101.46 |
| Solubilization speed (min) | 30 | 30 | 50 | 60* | 60* | 50 |
| Final formulation appearance | o | o | o | o | o | o |
| Lens appearance | o | o | o | x | x | o |
| Tv (%) | 89.5 | 89.3 | 89.5 | 88.8 | 89.4 | 89.5 |
| T (%) at 430 nm | 76 | 71 | 67 | 57 | 61 | 70 |
| Light cut-off (nm) | 410 | 412 | 414 | 417 | 415 | 396 |
| YI | 7.1 | 8.7 | 10.1 | 12.3 | 11.3 | 1.8 |

*At 30° C.

For polythiourethane matrix, solubility during processing and compatibility of inventive and comparative benzotriazoles were assessed in two stages. First, initial solubilization of the benzotriazole UV absorber in the isocyanate monomer was assessed. In formulations containing an inventive absorber (examples 1-5), full dissolution occurred very quickly within 4 to 10 min, whereas in non-inventive formulations (comparative examples C1-06), dissolution time was much longer (between 30 and 60 min). Heating was even necessary to keep dissolution time within reasonable duration (preparation <1 day) for comparative examples C4 and C5. Inventive benzotriazole IV, which only differs from comparative benzotriazole VII by the replacement of the ester chain with a methyl group, clearly has improved dissolution properties.

Second, behavior after thiol monomers addition was investigated by observing the aspect of final formulation, in particular the absence of precipitation (o indicates no precipitation). Formulations in which precipitation occurred were discarded. This may happen if the concentration in UV absorber is too large, typically above 2.5%

Example 5 reveals that the presence of the ester group is also beneficial in non chlorinated absorbers, and a comparison of examples 1 and 5 shows that the chlorinated benzotriazole IV (example 1) provides a higher light cut-off wavelength and a better blue light cut level at 430 nm than the corresponding non-chlorinated benzotriazole V. However, lenses obtained with example 5 are well balanced between protection against blue light (light cut at 400 nm) and cosmetic appearance (YI=2.5, much lower than lenses from examples 1 to 4).

When thiol parts THIOL1 and THIOL2 were added, polarity increased but did not cause precipitation in the inventive formulations. Comparative compositions did not show precipitation upon thiol parts THIOL1 and THIOL2 addition, but some homogeneous liquid formulations led to heterogeneity in the final lenses (shown with a X in tables), which were blurred (comparative examples C4 and C5), although comparable levels of benzotriazoles were used. The optical article of example 4 is similar to that of example 1, but contains more bluing agent in order to optimize color balancing, resulting in a lower yellowness index.

As shown in the tables above and FIG. 1, all the lenses prepared had a high transmission in the visible spectrum (Tv>87.5%, without any antireflective coatings), a high light cut-off wavelength 400 nm), offered protection from UV light and interesting blue light cut levels in 400 nm-430 nm range.

Examples 5 and C6 use similar benzotriazole compounds, except that example 5 uses a benzotriazole having an ester group. Solubilization speed and light cut off are improved in example 5, as compared to comparative example C6, demonstrating the importance of ester group on benzotriazole.

Examples 1 to 4 and C1 to C3 use similar chlorobenzotriazole, except that examples 1 to 4 use a benzotriazole having an ester group. Solubilization speed is clearly improved (lower than 5 minutes, as compared to larger than 30 minutes for C1 to C3). In addition, for a same light cut off value, examples 1 to 4 show better transmittance at 430 nm and lower Yellow Index. For light cut off of 410 nm, transmittance of example 2 is 78% at 430 nm (YI=6.9), compared to 76% at 430 nm in C1 (YI=7.1). For light cut off of 412 nm, transmittance of example 3 is 75% at 430 nm (YI=7.8), compared to 71% at 430 nm for C2 (YI=8.7). Finally, lenses obtained with examples 1 to 4 are well balanced between protection against blue light (light cut at 400 nm) and cosmetic appearance (low YI).

The invention claimed is:
1. An optical material comprising a polymer matrix and at least one benzotriazole compound having at least one ester group, wherein:
said at least one benzotriazole is a chlorobenzotriazole compound that does not comprise any polymerizable group selected from allylic, acrylic and methacrylic moieties, or
the optical transmittance through a 2 mm thick layer of said optical material is lower than 1% for each light wavelength ranging from 280 to 400 nm, and higher than 65% for light having a wavelength of 430 nm.

2. The optical material of claim 1, wherein the optical transmittance through a 2 mm thick layer of said material is lower than 1% for light having a wavelength ranging from 280 to 405 nm, and higher than 65% for light having a wavelength of 430 nm.

3. The optical material of claim 1, wherein said at least one benzotriazole is a compound of formula (I) that does not comprise any polymerizable group selected from allylic, acrylic and methacrylic moieties:

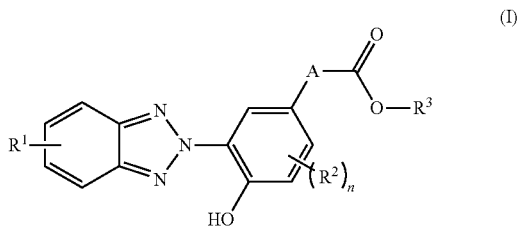

(I)

in which A is a divalent group, $R^1$ is a resonant group or a hydrogen atom, the $R^2$ groups are identical or different monovalent groups, n is an integer ranging from 1 to 3, and $R^3$ is a linear or branched, substituted or unsubstituted alkyl or aryl group.

4. The optical material of claim 3, wherein $R^1$ is a resonant group selected from halogen, cyano, amino, hydroxyl, mercapto, carboxy, alkoxy, aryloxy, alkylsulfanyl and arylsulfanyl.

5. The optical material of claim 4, wherein $R^1$ is a halogen atom in position 4 or 5 on the aryl group.

6. The optical material of claim 3, wherein A is a substituted or unsubstituted linear or branched alkylene group comprising from 1 to 6 carbon atoms.

7. The optical material of claim 3, wherein the $R^2$ groups are independently selected from a hydrogen atom and linear or branched, substituted or unsubstituted hydrocarbon groups comprising from 1 to 6 carbon atoms.

8. The optical material of claim 3, wherein $R^3$ is a linear or branched, substituted or unsubstituted alkyl group comprising from 1 to 14 carbon atoms.

9. The optical material of claim 3, wherein n=1, $R^2$ is a linear or branched alkyl group comprising from 1 to 6 carbon atoms, $R^3$ is a linear or branched alkyl group comprising from 1 to 10 carbon atoms, and A is a linear alkylene group comprising from 1 to 4 carbon atoms.

10. The optical material of claim 1, further defined as being the substrate of an optical lens, preferably an ophthalmic lens.

11. The optical material of claim 1, further defined as being the substrate of an ophthalmic lens.

12. The optical material of claim 1, wherein said benzotriazole compounds are present in an amount ranging from 0.2 to 3.0% by weight relative to the optical material total weight.

13. The optical material of claim 1, wherein the polymer matrix is obtained from a thermosetting resin comprising bis(2,3-epithiopropyl)disulfide and a mixture of (4,8) or (4,7) or (5,7)-dimercaptomethyl-1,11-dimercapto-3,6,9-trithiaundecane.

14. A method for preparing an optical material of claim 1, comprising:
    obtaining a polymerizable composition comprising at least one ultraviolet-absorbing benzotriazole compound having at least one ester group, and at least one polymerizable compound,
    curing said polymerizable composition so as to form the optical material comprising a polymer matrix and said at least one benzotriazole compound having at least one ester group,
wherein:
    said at least one benzotriazole is a chlorobenzotriazole compound that does not comprise any polymerizable group selected from allylic, acrylic and methacrylic moieties, or
    optical transmittance through a 2 mm thick layer of said optical material is lower than 1% for each light wavelength ranging from 280 to 400 nm, and higher than 65% for light having a wavelength of 430 nm.

15. The method of claim 14, wherein a homogeneous polymerizable composition is obtained at 25° C. in less than 20.

16. The method of claim 14, wherein said at least one polymerizable compound is selected from allyl glycol carbonates, polythiols, episulfides, polyisocyanates, polyisothiocyanates and (meth)acrylates.

* * * * *